(12) United States Patent
Uhlemann et al.

(10) Patent No.: US 11,609,294 B2
(45) Date of Patent: Mar. 21, 2023

(54) ACQUISITION OF FOUR DIMENSIONAL MAGNETIC RESONANCE DATA DURING SUBJECT MOTION

(71) Applicant: KONINKLIJKE PHILIPS N.V., Eindhoven (NL)

(72) Inventors: Falk Uhlemann, Hamburg (DE); Tim Nielsen, Hamburg (DE); Jan Hendrik Wuelbern, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 750 days.

(21) Appl. No.: 16/479,802

(22) PCT Filed: Jan. 23, 2018

(86) PCT No.: PCT/EP2018/051610
§ 371 (c)(1),
(2) Date: Jul. 22, 2019

(87) PCT Pub. No.: WO2018/134445
PCT Pub. Date: Jul. 26, 2018

(65) Prior Publication Data
US 2021/0325500 A1    Oct. 21, 2021

Related U.S. Application Data

(60) Provisional application No. 62/504,706, filed on May 11, 2017.

(30) Foreign Application Priority Data

Jan. 23, 2017   (EP) ..................................... 17152549

(51) Int. Cl.
*G01R 33/56*      (2006.01)
*G01R 33/563*     (2006.01)
(Continued)

(52) U.S. Cl.
CPC ... *G01R 33/56325* (2013.01); *G01R 33/5608* (2013.01); *G01R 33/5676* (2013.01);
(Continued)

(58) Field of Classification Search
CPC ..... A61B 5/055; A61B 5/0037; A61B 5/7285; G01R 33/56325; G01R 33/5676
See application file for complete search history.

(56) References Cited

U.S. PATENT DOCUMENTS 6,198,959 B1 *  3/2001  Wang ................... A61B 5/0037
                                                    324/309
7,782,053 B2     8/2010  Kanda
                         (Continued)

FOREIGN PATENT DOCUMENTS

EP          3118644 A1 *  7/2016 ........... G01R 33/567
WO    WO2015121103 A1    8/2015
                         (Continued)

OTHER PUBLICATIONS

PCT International Search Report, International application No. PCT/EP2018/051610, dated Jun. 27, 2018.
(Continued)

*Primary Examiner* — James M Kish

(57) ABSTRACT

The invention provides for a magnetic resonance imaging system (100, 200) comprising a memory (148) for storing machine executable instructions (150) and pulse sequence commands (152). The pulse sequence commands are configured for acquiring a four dimensional magnetic resonance data set (162) from an imaging region of interest (109). The four dimensional magnetic resonance data set is at least divided into three dimensional data magnetic resonance data sets (400, 402, 404, 406, 408) indexed by a repetitive motion phase of the subject. The three dimensional data magnetic
(Continued)

resonance data sets are further at least divided into and indexed by k-space portions (410, 412, 414, 416, 418, 420, 422, 424, 426, 428, 430, 432, 434, 436). The magnetic resonance imaging system further comprises a processor (144) for controlling the magnetic resonance imaging system. Execution of the machine executable instructions causes the processor during a first operational portion (310) to iteratively: receive (300) a motion signal (156) descriptive of the repetitive motion phase; acquire (302) an initial k-space portion using the pulse sequence commands, wherein the initial k-space portion is selected from the k-space portions; store (304) the motion signal and the initial k-space portion in a buffer (158) for each iteration of the first operational portion; at least partially construct (306) a motion phase mapping (160) between the motion signal and the repetitive motion phase; and continue (308) the first operational portion until the motion phase mapping is complete. Execution of the machine executable instructions causes the processor to assign (312) the initial k-space portion for each iteration of the first operational portion in the temporary buffer to the four dimensional magnetic resonance data set using the motion phase mapping. Execution of the machine executable instructions causes the processor during a second operational portion (332) to iteratively: receive (314) the motion signal; determine (316) a predicted next motion phase using the motion signal and the motion phase mapping; select (318) a subsequent k-space portion (154) from the k-space portions of the four dimensional magnetic resonance data set using the predicted next motion phase; acquire (320) the subsequent k-space portion using the pulse sequence commands; rereceive (322) the motion signal; determine (324) a current motion phase using the re-received motion signal and the motion phase mapping; assign (326) the subsequent k-space portion to the four dimensional magnetic resonance data set using the current motion phase; and repeat (328) the second operational portion until the k-space portions for each repetitive motion phase has been assigned.

19 Claims, 6 Drawing Sheets

(51) Int. Cl.
*G01R 33/567* (2006.01)
*A61B 5/055* (2006.01)
*A61B 5/00* (2006.01)

(52) U.S. Cl.
CPC ............ *A61B 5/0037* (2013.01); *A61B 5/055* (2013.01); *A61B 5/7285* (2013.01)

(56) References Cited

U.S. PATENT DOCUMENTS

| | | | |
|---|---|---|---|
| 9,366,742 | B2 | 6/2016 | Kramer |
| 2006/0183999 | A1* | 8/2006 | Lorenz ............... G01R 33/5673 600/410 |
| 2006/0224062 | A1 | 10/2006 | Aggarwal |
| 2007/0090837 | A1 | 4/2007 | Van Der Kouwe |
| 2012/0245453 | A1 | 9/2012 | Tryggestad |
| 2015/0123659 | A1 | 5/2015 | Weingartner |
| 2016/0310038 | A1 | 10/2016 | Hu |
| 2017/0016972 | A1 | 1/2017 | Bhat |
| 2017/0139026 | A1* | 5/2017 | Beck .................... A61B 5/7207 |
| 2021/0048497 | A1 | 2/2021 | Nimbargi |

FOREIGN PATENT DOCUMENTS

| | | |
|---|---|---|
| WO | WO2016023910 A1 | 2/2016 |
| WO | WO2016124763 A1 | 8/2016 |

OTHER PUBLICATIONS

Observations on the PCT International Search Report and the Written Opinion of International Application No. PCT/EP2018/051610, dated Jul. 23, 2018.

Peng Hu et al: "Motion Correction Using Coil Arrays (MOCCA) for Free-Breathing Cardiac Cine MRI", Magnetic Resonance in Medicine., vol. 66, No. 2, Feb. 24, 2011 (Feb. 24, 2011), pp. 467-475, XP055411170.

Tanner C. et al., "Improved Reconstruction of 4DMR Images", Motion Predictions, Medical Image Computing and Computer-Assisted Intervention—MICCAI 2014, vol. 8673 of the series Lecture Notes in Computer Science, pp. 146-153.

Seregni M. et al., "Motion prediction in MRI-guided radiotherapy based on interleaved orthogonal cine-MRI", Institute of Physics and Engineering in Medicine, Physics in Medicine and Biology, vol. 61, No. 2, Jan. 7, 2016.

Celicanin Z. et al., "Simultaneous acquisition of image and navigator slices using CAIPIRINHA", Proc. Intl. Soc. Mag. Reson. Med. 19 (2011), p. 4399.

Yang W. et al., "Four-Dimensional Magnetic Resonance Imaging With 3-Dimensional Radial Sampling and Self-Gating-Based K-Space Sorting: Early Clinical Experience on Pancreatic Cancer Patients", International Journal of Radiation Oncology,Biology, Physics,vol. 93, No. 5, pp. 1136-1143, 2015.

Zhong W. et al., "Image Reconstruction and Registration of Liver 4D Dynamic Contrast-Enhanced Magnetic Resonance Imaging", Medicine and Health Technology Collection of China Master's Theses Full-text Database, vol. 1, 2017.

* cited by examiner

ACQUISITION OF FOUR DIMENSIONAL MAGNETIC RESONANCE DATA DURING SUBJECT MOTION

CROSS REFERENCE TO RELATED APPLICATIONS

This patent application claims the priority benefit under 35 U.S.C. § 371 of International Patent Application no. PCT/EP2018/051610, filed Jan. 23, 2018, which claims the benefit of European Patent Application No. EP17152549.6, filed on Jan. 23, 2017, and which also claims the benefit of U.S. Application Ser. No. 62/504,706, filed on May 11, 2017. These applications are hereby incorporated by reference herein in their entirety.

TECHNICAL FIELD

The invention relates to magnetic resonance imaging, in particular to magnetic resonance imaging techniques for imaging repetitive motion of a subject.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the B0 field.

During an MRI scan, Radio Frequency (RF) pulses generated by a transmitter coil or antenna causes perturbations to the local magnetic field, and RF signals emitted by the nuclear spins are detected by a receiver coil. These RF signals are used to construct the MRI images. Movement of a subject during a MRI procedure can cause artifacts or errors in the resulting image. If the motion of a subject is periodic, the acquisition of the magnetic resonance data can be synchronized with the subjects motion and a four dimensional magnetic resonance image can be acquired that images the periodic motion of the subject. A four dimensional magnetic resonance image is a time series of three dimensional magnetic resonance images.

International patent application WO 2015/121103 A1 discloses, 1 method of operating a respiratory-guided magnetic resonance imaging system with regard to triggering of magnetic resonance image acquisition, the magnetic resonance imaging system being connectable to a respiration monitoring device which is configured to provide an output signal whose level represents a respiration state of the subject of interest, the method comprising a step of generating an interleaved acquisition scheme for acquiring magnetic resonance images, a step of adapting, in case of an occurrence of an irregularity in the breathing of the subject of interest in the output signal obtained by the respiration monitoring device in the course of executing magnetic resonance image acquisition, at least one parameter of the interleaved acquisition scheme, wherein the at least one adapted parameter is at least one of a next respiration state of the subject of interest to trigger on for acquiring at least one magnetic resonance image, a radio frequency pulse sequence-inherent idle time, and the chronological order of at least one slice of the plurality of slices to be imaged of at least the portion of the subject of interest, a step of halting execution of magnetic resonance image acquisition, and a step of resuming or continuing execution of magnetic resonance image acquisition pursuant to the interleaved acquisition scheme using the adapted parameter; a respiratory-guided magnetic resonance imaging system having a control unit that is configured to carry out steps of an embodiment of the disclosed method; and a software module for carrying out an embodiment of the disclosed method, wherein the method steps to be conducted are converted into a program code that is implementable in a memory unit and is executable by a processor unit of the respiratory-guided magnetic resonance imaging system.

US 2006/0183999 A1 discloses a method and system provided for imaging by predicting, from multiple real time MR imaging data, motion of an object. When a motion model is complete, this model is used to predict when the motion state occurs for which high resolution images will be acquired.

SUMMARY OF THE INVENTION

The invention provides for a magnetic resonance imaging system, a computer program product, and a method in the independent claims. Embodiments are given in the dependent claims.

Embodiments may provide for an accelerated means of acquiring a four dimensional magnetic resonance imaging data set that may be used for imaging preferably repetitive motion of a subject. A four dimensional magnetic resonance imaging data set is a collection of three dimensional magnetic resonance imaging data sets that form a time series. A three dimensional magnetic resonance imaging data set comprises magnetic resonance data acquired for a three dimensional region of interest or a series of two dimensional slices that can be used to form a three dimensional volume. Embodiments of the invention may provide for accelerated acquisition of the four dimensional data set by dividing the acquisition into two operational portions. During the first operational portion magnetic resonance data is acquired in the form of initial k-space portions while a motion signal descriptive of the repetitive motion of the subject is acquired. Over time a motion phase mapping is built up which can be used to map the motion signal to the repetitive motion phase of the subject. The initial k-space portions acquired during the building of the motion phase mapping are then assigned or copied to the proper location within the four dimensional magnetic resonance data set. The magnetic resonance imaging system is therefore able to acquire a portion of the four dimensional magnetic resonance data set before the motion phase mapping is complete. This saves some time.

Motion phase mapping could be achieved in multiple ways. For example this can be done by computing a 2D histogram for pairs of subsequent motion states which have been observed so far. Instead of 2D histograms also longer sequences of motion states could be used to predict a subsequent motion phase. In addition to that, other alternatives, like e.g. Bayesian inference networks could be used.

The magnetic resonance imaging system then begins the second operational phase. During the second operational phase the motion signal from at least the previous acquisition is used to predict the repetitive motion phase of the subject during the next acquisition. The pulse sequence commands for the next acquisition can then be tailored so that they acquire k-space portions of the four dimensional data set that have not yet been acquired for a respective motion phase. This enables the complete four dimensional magnetic resonance data set to be acquired efficiently.

In one aspect, the invention provides for a magnetic resonance imaging system comprising a memory for storing machine-executable instructions and pulse sequence commands. Pulse sequence commands as used herein encompass either data which can be used directly or which can be transformed into instructions which can be used to control the magnetic resonance imaging system to acquire magnetic resonance data. The pulse sequence commands are configured for acquiring a four-dimensional magnetic resonance dataset from an imaging region of interest. Four-dimensional magnetic resonance data as used herein encompasses a collection of three-dimensional magnetic resonance datasets that are acquired in a time series or at different times. Three-dimensional magnetic resonance data may encompass data acquired for a collection of two-dimensional slabs or voxels or data which is descriptive of a three-dimensional volume.

The acquisition of the four-dimensional magnetic resonance dataset is divided into three dimensional data magnetic resonance data sets indexed by repetitive motion phase of the subject. The repetitive motion phase of the subject provides for the temporal dimension in the four-dimensional magnetic resonance dataset. The time dimension is indexed to a repetitive motion phase of the subject such as breathing. The three dimensional data magnetic resonance data sets of the four-dimensional magnetic resonance dataset is further at least divided into and indexed by k-space portions. The k-space portions indicate particular locations in k-space which are acquired during one of the three dimensional data magnetic resonance data sets. In different examples the k-space portions could be interpreted differently. In one example a particular k-space portion represents a particular slice. The acquisition of the various k-space portions may then provide for the slices which are used to make the three-dimensional dataset which is then combined with the repetitive motion phase to form the four-dimensional magnetic resonance dataset. The k-space portions could also be part of a three-dimensional magnetic resonance dataset or could also be a part of a two-dimensional dataset for a slice.

The magnetic resonance imaging system further comprises a processor for controlling the magnetic resonance imaging system. Execution of the machine-executable instructions causes the processor during a first operational portion to iteratively receive a motion signal descriptive of the repetitive motion phase. A motion signal as used herein encompasses data which is descriptive of a repetitive motion of a subject. This may take many different forms. For example such things as cameras or respiration belts, or even magnetic resonance navigators may be used to drive all or part of a motion signal. In some examples different types of data may be used to provide a composite motion signal that comprises such things as camera data and/or respirator belt data and/or magnetic resonance navigator data. By performing operator instructions iteratively it is meant that these may be performed multiple times. Execution of the machine-executable instructions further cause the processor during the first operational portion to iteratively acquire an initial k-space portion using the pulse sequence commands.

The initial k-space portion is selected from the k-space portions. Execution of the machine-executable instructions further causes the processor during the first operational portion to iteratively store the motion signal and the initial k-space portion in a temporary buffer for each iteration of the first operational portion. Execution of the machine-executable instructions further causes the processor during the first operational portion to iteratively at least partially construct a motion phase mapping between the motion signal and the repetitive motion phase. Execution of the machine-executable instructions further causes the processor during the first operational portion to iteratively continue the first operational portion until the motion phase mapping is complete.

During the first operational portion the magnetic resonance imaging system is controlled such that it acquires the motion signal and at the same time is acquiring initial k-space portions. However at this time it is not yet known how the motion signal is related exactly to the repetitive motion phase of the subject. The k-space portion is therefore stored in a temporary buffer with the motion signal for later use.

Execution of the machine-executable instructions further causes the processor to assign the initial k-space portion for each iteration of the first operational portion in the temporary buffer to the four-dimensional magnetic resonance dataset using the motion phase mapping. Once the motion phase mapping is complete the data which has been stored in the buffer may then be assigned to the four-dimensional magnetic resonance dataset.

Execution of the machine-executable instructions further causes the processor during a second operational portion to iteratively receive the motion signal. Execution of the machine-executable instructions further cause the processor during the second operational portion to iteratively determine a predicted next motion phase using the motion signal and the motion phase mapping. Execution of the machine-executable instructions further causes the processor during the second operational portion to iteratively select a subsequent k-space portion from the k-space portions of the four-dimensional magnetic resonance dataset using the predicted next motion phase. The subsequent k-space portion may for instance be one that has not yet been acquired for a specific motion phase. If all of the data for a particular repetitive motion phase has been acquired the data may be acquired for e.g. averaging.

Execution of the machine-executable instructions further causes the processor during the second operational portion to iteratively acquire the subsequent k-space portion using the pulse sequence commands to control the magnetic resonance imaging system. Execution of the machine-executable instructions further causes the processor during the second operational portion to iteratively re-receive the motion signal. Execution of the machine-executable instructions further causes the processor during the second operational portion to iteratively determine a current motion phase using the re-received motion signal and the motion phase mapping. Execution of the machine-executable instructions further causes the processor during the second operational portion to iteratively assign the subsequent k-space portion to the four-dimensional magnetic resonance dataset using the current motion phase. Execution of the machine-executable instructions further causes the processor during the second operational portion to iteratively repeat the second operational portion until the k-space portion for each repetitive motion phase has been acquired/assigned. The re-received motion signal is used for determining the predicted next motion phase.

In the second operational portion, the motion phase mapping has been completed. The motion signal may therefore then be used to predict what the next motion phase of the subject will be. The processor can then acquire a subsequent k-space portion that has not previously been acquired using this prediction. When the subsequent k-space portion is acquired the re-received motion signal is used to confirm that the k-portion was acquired for the proper or expected motion phase of the subject. The subsequent k-space portion may then be assigned to the four-dimensional magnetic resonance dataset using the current motion phase. This process is then repeated until all of the four-dimensional magnetic resonance dataset is acquired.

This embodiment may have the benefit that it provides for an extremely efficient way of acquiring the magnetic resonance data for a four-dimensional magnetic resonance dataset.

In another embodiment, the calculation of the predicted next motion phase is based on the transition probability of motion phases as recorded in previous iterations. This method assumes that the prediction can be performed faster than the duration of one imaging iteration, enabling the same timing for image acquisition and processing during operational portion one, when the initial transition probabilities are recorded, and operational portion two, when the transition probabilities are used and refined to predict the next motion phase.

In another embodiment, the calculation of a future (after the next) motion phase is also based on the transition probability of motion phases as recorded in previous iterations. This method does not assume that the transition prediction can be performed faster than the duration of one imaging iteration but that the transition probability over more than two imaging iterations still yields reliable predictions.

In another embodiment, the fundamental frequency of the repetitive motion is used for the prediction of the next motion phase. Assuming a more or less constant motion with a respective fundamental frequency f, e.g. a regular breathing motion, the temporal distance between the last received motion phase and a motion phase in the future can be predicted by employing the knowledge about the duration of one full motion cycle, i.e. 1/f. This allows to calculate the time between the current motion phase and a certain required/missing motion phase and control the imaging system in such a way as to specifically acquire a portion of the k-space at the calculated time. The received motion signal has then to be used to verify the validity of the prediction, as in all above mentioned methods.

In another embodiment, the pulse sequence commands are configured to control the magnetic resonance imaging system to acquire two-dimensional magnetic resonance imaging navigator data from a navigator region of interest using the pulse sequence commands. As used herein two-dimensional magnetic resonance imaging navigator data is magnetic resonance data that may be used for a two-dimensional navigator technique. As used herein a navigator region of interest is a region of interest. The navigator region of interest is a specific label for a particular region of interest. The navigator region of interest is larger than or equally large as the imaging region of interest. The navigator region of interest comprises the imaging region of interest. The receiving of the motion signal descriptive of the repetitive motion phase comprises at least partially calculating the motion signal using the two-dimensional magnetic resonance imaging navigator data. This embodiment may be beneficial because the navigator region of interest is the same size or larger than the imaging region of interest. The signal from the navigator region of interest may therefore have a large signal to noise ratio. Additionally, when the navigator region of interest is the same size or larger than the imaging region of interest there is no need to specifically place it or place it in the correct location. There is therefore no need to specifically align a magnetic resonance imaging navigator within the imaging region of interest.

The two-dimensional magnetic resonance imaging navigator data could for example either be acquired before or after the initial k-space portion or the subsequent k-space portion.

In some examples, the navigator region of interests may be the same size as or larger than the imaging region of interest. The navigator region of interest takes the data from this region and condenses it to a two-dimensional (2D) magnetic resonance navigator image. The slice thickness is therefore equivalent to one of the dimensions of the navigator region of interest. The resulting slice thickness (or voxel size in the direction of the slice thickness of the two-dimensional magnetic resonance navigator image) for images reconstructed from the four dimensional magnetic resonance data set will be will be less than the slice thickness of the two-dimensional magnetic resonance navigator image.

In another embodiment, the navigator region of interest is larger than the imaging region of interest.

In another embodiment, the calculation of the motion signal using the two-dimensional magnetic resonance imaging navigator data comprises reconstructing a two-dimensional navigator image using the two-dimensional magnetic resonance imaging navigator data. The calculation of the motion signal using the two-dimensional magnetic resonance imaging navigator data further comprises calculating a navigator registration by registering the two-dimensional navigator image to at least one other two-dimensional navigator image from another iteration of the other iterations of the first or second operational portion. The calculation of the motion signal using the two-dimensional magnetic resonance imaging navigator data further comprises calculating the motion signal at least partially using the navigator registration. For example, a particular two-dimensional navigator image from the first operational portion may be designated as a base and then the registration of the other images may be used to calculate the motion signal. The registration for example could be a mapping from the one two-dimensional navigator image to a different two-dimensional navigator image. Vectors or other data from specific portions or the entire two-dimensional navigator image mapping might be used. This embodiment may have the advantage that it is extremely easy to use this large two-dimensional navigator image instead of a precisely placed navigator.

In another embodiment, the two-dimensional navigator image has a lower resolution than an image reconstructed from the four-dimensional magnetic resonance dataset.

In another embodiment, the magnetic resonance imaging system comprises an imaging volume. The navigator region of interest is equivalent to the imaging volume. The imaging volume as used herein encompasses a region where the magnetic field is uniform enough that magnetic resonance imaging can be performed. By making the entire imaging volume the navigator region of interest and projecting it onto a two-dimensional plane, a large signal-to-noise ratio can be achieved for a relatively low resolution image of the entire imaging volume. This may provide for a method which is able to capture the gross or large-scale motion of the subject completely and robustly and in a manner which does not need pre-configuration of the navigator. The registration of these two-dimensional navigator images to each other may eliminate the need to precisely place a navigator.

In another embodiment, the 2D magnetic resonance imaging navigator data is always recorded immediately before the initial k-space portion and/or the subsequent k-space portion in a constantly repeated and interleaved fashion. If the recording of the 2D magnetic resonance imaging navigator data and the initial and/or subsequent k-space portion is fast enough, i.e. the change of the motion state is small during the acquisition, it can be assumed that the motion phase according to the navigator signal and the phase of the initial and/or subsequent k-space portion are the same.

In another embodiment 2D magnetic resonance imaging navigator data is also recorded immediately before the initial and/or subsequent k-space portion in a constantly repeated interleaved fashion. Assuming a constant repetitive motion, i.e. that a certain motion phase of the navigator corresponds to a certain motion phase of the initial and/or subsequent k-space portion, this correspondence knowledge can be used to assign the "true" motion phase to the initial and/or subsequent k-space portion based on the preceding navigator motion phase and the time between the recording of the navigator and the k-space data.

In another embodiment, single or multiple 2D magnetic resonance imaging navigator data sets are recorded immediately before and optionally immediately after the partial k-space data in a constantly repeated interleaved fashion. Employing linear or non-linear interpolation of motion phases, in case navigators are recorded before and after, or extrapolation, in case navigators are recorded before only, the motion state of the adjacent partial k-space data can be calculated and assigned.

In another embodiment the above mention methods are employed, but in a controlled acquisition scheme, i.e. a possibly irregular, instead of a constantly repeated fashion. This control is based on a motion model and the respective predicted acquisition time for a specific required/missing motion phase.

In another embodiment, the navigator region of interest comprises a two-dimensional span. The navigator region of interest comprises a thickness perpendicular to the two-dimensional span. The thickness is greater than any one of the following: 30 cm, 35 cm, and 40 cm. This embodiment may be beneficial because the measured magnetic resonance signal (the measured 2D magnetic resonance imaging navigator data) for the navigator may be relatively large, which results in a large signal to noise ratio. This means that the magnetic resonance signal can be acquired very rapidly and with a low flip angle that will have a low effect on subsequent magnetic resonance imaging techniques.

In another embodiment, the motion signal comprises any one of the following: camera data, one-dimensional MRI navigator data, two-dimensional navigator data, respiration monitor belt data, tensile navigator data, and combinations thereof. This embodiment may be beneficial because one or more conventional navigators may be combined together to provide the motion signal.

In another embodiment, the magnetic resonance imaging system further comprises a camera for acquiring the camera data.

In another embodiment, the magnetic resonance imaging system further comprises a respiration monitor belt system for acquiring the respiration monitor belt data.

In another embodiment, the current motion phase is determined using a trajectory calculated from the motion signal data received during previous iterations of the second operational portion. For example, the motion phase mapping may not use just specifically the current data but also motion data that has been previously acquired in previous iterations. This may allow the use of a trend or velocity in the motion signal to help better predict the subsequent or predicted next motion phase of the subject.

In another embodiment, the repetitive motion phase comprises a respiratory phase of the subject.

In another embodiment, the k-space portion is any one of the following: k-space data for a two-dimensional slice, a portion of k-space data for a two-dimensional slice, a portion of k-space data for a three-dimensional volume.

In another embodiment, the assignment of the subsequent k-space portion for each iteration of the second operational portion to the four-dimensional magnetic resonance dataset comprises any one of the following: copying the subsequent k-space portion to the four-dimensional magnetic resonance dataset, averaging the subsequent k-space portion with existing data in the four-dimensional magnetic resonance dataset, and replacing existing data in the four-dimensional magnetic resonance dataset, and also possibly ignoring the subsequent k-space portion.

In another embodiment, the assignment of the initial k-space portion from each iteration of the first operational portion in the temporary buffer to the four-dimensional magnetic resonance dataset using the motion phase mapping comprises any one of the following: copying the initial k-space portion to the four-dimensional magnetic resonance dataset, averaging the initial k-space portion with the existing data in the four-dimensional magnetic resonance dataset, replacing the existing data in the four-dimensional magnetic resonance dataset, and ignoring the initial k-space portion.

In another embodiment, the initial k-space portion is selected according to a predetermined sequence.

In another embodiment, the k-space portion is selected at random. Both this embodiment and also the previous embodiment where the k-space portion is selected according to a predetermined sequence may be beneficial because it may reduce the chance that a particular k-space portion for the same repetitive motion phase of the subject is acquired during the first operational portion. This may have the effect of accelerating the acquisition of the four-dimensional magnetic resonance dataset.

In another aspect, the invention provides for a computer program product comprising machine-executable instructions for execution by a processor controlling the magnetic resonance imaging system. Execution of the machine-executable instructions causes the processor during a first operational portion to iteratively receive a motion signal descriptive of a repetitive motion phase of the subject. Execution of the machine-executable instructions further causes the processor during the first operational portion to iteratively acquire an initial k-space portion using pulse sequence commands to control the magnetic resonance imaging system. The pulse sequence commands are configured for acquiring a four-dimensional magnetic resonance dataset from an imaging region of interest. The acquisition of the four-dimensional magnetic resonance dataset is at least divided into three dimensional data magnetic resonance data sets indexed by a repetitive motion phase of the subject. The three dimensional data magnetic resonance data sets of the four-dimensional magnetic resonance dataset is further at least divided into and indexed by k-space portions.

The initial k-space portion is selected from the k-space portions. Execution of the machine-executable instructions further causes the processor during the first operational portion to iteratively store the motion signal and the initial k-space portion in a buffer for each iteration of the first operational portion. Execution of the machine-executable instructions further causes the processor during the first operational portion to iteratively at least partially construct a motion phase mapping between the motion signal and the repetitive motion phase. Execution of the machine-executable instructions further causes the processor during the first operational portion to iteratively continue the operational portion until the motion phase mapping is complete.

Execution of the machine-executable instructions further cause the processor to assign the initial k-space portion for each iteration of the first operational portion in the buffer to the four-dimensional magnetic resonance dataset using the motion phase mapping. Execution of the machine-executable instructions further cause the processor during a second operational portion to iteratively receive the motion signal. Execution of the machine-executable instructions further cause the processor during the second operational portion to iteratively determine a predicted next motion phase using the motion signal and the motion phase mapping. Execution of the machine-executable instructions further causes the processor during the second operational portion to iteratively select a subsequent k-space portion from the k-space portions of the four-dimensional magnetic resonance dataset using the predicted next motion phase.

Execution of the machine-executable instructions further causes the processor during the second operational portion to iteratively acquire the subsequent k-space portion using the pulse sequence commands. Execution of the machine-executable instructions further cause the processor during the second operational portion to iteratively re-receive the motion signal. Execution of the machine-executable instructions further cause the processor during the second operational portion to iteratively determine a current motion phase using the re-received motion signal and the motion phase mapping. Execution of the machine-executable instructions further causes the processor during the second operational portion to iteratively assign the subsequent k-space portion to the four-dimensional magnetic resonance dataset using the current motion phase. Execution of the machine-executable instructions further causes the processor during the second operational portion to iteratively repeat the second operational portion until the k-space portions for each of the repetitive motion phases has been assigned. The re-received motion signal is used for determining the predicted next motion phase.

In another aspect, the invention provides for a method for operating a magnetic resonance imaging system. The method comprises during a first operational portion iteratively receiving a motion signal descriptive of a repetitive motion phase of a subject. The method comprises, during the first operational portion, iteratively acquiring an initial k-space portion using pulse sequence commands to control a magnetic resonance imaging system. The pulse sequence commands are configured for acquiring a four-dimensional magnetic resonance dataset from an imaging region of interest. The acquisition of the four-dimensional magnetic resonance dataset is at least divided into three dimensional data magnetic resonance data sets indexed by a repetitive motion phase of the subject. The three dimensional data magnetic resonance data sets of the four-dimensional magnetic resonance dataset is further at least divided into and indexed by k-space portions. The initial k-space portion is selected from the k-space portions.

The method further comprises, during the first operational portion, iteratively storing the motion signal and the initial k-space portion in a buffer for each iteration of the operational portion. The method further comprises, during the first operational portion, iteratively at least partially constructing a motion phase mapping between the motion signal and the repetitive motion phase. The method further comprises, during the first operational portion, iteratively continuing the first operational portion until the motion phase mapping is complete. The method further comprises assigning the initial k-space portion for each iteration of the first operational portion in the buffer to the four-dimensional magnetic resonance dataset using the motion phase mapping.

The method further comprises, during a second operational portion, iteratively receiving the motion signal. The method further comprises, during the second operational portion, iteratively determining a predicted next motion phase using the motion signal and the motion phase mapping. The method further comprises, during the second operational portion, iteratively selecting a subsequent k-space portion from the k-space portions of the four-dimensional magnetic resonance dataset using the predicted next motion phase. The method further comprises, during the second operational portion, iteratively acquiring the subsequent k-space portion using the pulse sequence commands. The method further comprises, during the second operational portion, iteratively re-receiving the motion signal. The method further comprises, during the second operational portion, iteratively determining a current motion phase using the re-received motion signal and the motion phase mapping. The method further comprises, during the second operational portion, iteratively assigning the subsequent k-space portion to the four-dimensional magnetic resonance dataset using the current motion phase. The method further comprises repeating the second operational portion until the k-space portions for each repetitive motion phase has been assigned. The re-received motion signal is used for determining the predicted next motion phase. The k-space portions acquired during the first operational portion and the k-space portions acquired during the second operational portion together form the four dimensional magnetic resonance imaging dataset, which can be used to reconstruct a 4D MRI image.

In another aspect, the invention provides for a magnetic resonance imaging system comprising a memory for storing machine-executable instructions and pulse sequence commands. The pulse sequence commands are configured for acquiring imaging magnetic resonance data from an imaging region of interest. The pulse sequence commands are further configured to control the magnetic resonance imaging system to acquire two-dimensional magnetic resonance imaging navigator data from a navigator region of interest using the pulse sequence commands. The navigator region of interest is the same size as or larger than the imaging region of interest. The navigator region of interest comprises the imaging region of interest. The magnetic resonance imaging system further comprises a processor for controlling the magnetic resonance imaging system. Execution of the machine-executable instructions causes the processor to iteratively acquire the two-dimensional magnetic resonance imaging navigator data and the imaging magnetic resonance data by controlling the magnetic resonance imaging system with the pulse sequence commands.

Execution of the machine-executable instructions further cause the processor to reconstruct a two-dimensional navigator image using the two-dimensional magnetic resonance imaging navigator data. Execution of the machine-executable instructions further causes the processor to calculate a navigator registration by registering the two-dimensional navigator image to at least one other two-dimensional navigator image from the previous iteration. Execution of the machine-executable instructions further cause the processor to calculate a motion signal at least partially using the navigator registration. Execution of the machine-executable instructions further cause the processor to assign the motion signal to the imaging magnetic resonance data.

In another embodiment, the magnetic resonance imaging system further comprises an imaging volume. The navigator region of interest is equivalent to the imaging volume.

In another embodiment, the navigator region of interest comprises a two-dimensional span. The navigator region of interest comprises a thickness perpendicular to the two-dimensional span. The two-dimensional span has a thickness perpendicular to the two-dimensional span. The thickness is greater than any one of the following: 30 cm, 35 cm, and 40 cm.

In another embodiment, the two-dimensional navigator image has a resolution of 128×128 voxels. In another embodiment the two-dimensional navigator image has a resolution between 100×100 voxels and 150×150 voxels.

In another embodiment, the pulse sequence commands are configured for acquiring the two-dimensional magnetic resonance imaging navigator data using a FFE Fast Gradient Echo magnetic imaging protocol. This embodiment may be beneficial because if you have a large signal you do not need to use a large flip angle to get the signal. An FFE pulse sequence generates an echo signal generated from a free induction decay by means of a bipolar switch magnetic gradient. This pulse sequence uses an excitation pulse. Typically in FFE pulse sequences the magnetization tilts the flip angle between 0° and 90°. However in this particular use a small flip angle can be used. In one embodiment the flip angle is <10°. In another embodiment the flip angle is <5°. In another embodiment the flip angle is <2°.

In another embodiment, the 2D navigator image is a sagittal or coronal plane of the subject. The plane could also be co-planar with a subject support of the magnetic resonance imaging system or perpendicular to the subject support passing through the z-axis of the magnet. The z-axis of the magnet is understood to be an axis of symmetry for the magnetic resonance field. In cylindrical magnets the z-axis typically passes through the center of the cylindrical magnet.

It is understood, that the various embodiments may be combined as long as they are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage may be any volatile or non-volatile computer-readable storage medium.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the C programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) display, Electroluminescent display (ELD), Plasma display panel (PDP), Liquid crystal display (LCD), Organic light-emitting diode display (OLED), a projector, and Head-mounted display.

Magnetic Resonance (MR) data is defined herein as being the recorded measurements of radio frequency signals emitted by atomic spins using the antenna of a magnetic resonance apparatus during a magnetic resonance imaging scan. Magnetic resonance data is an example of medical imaging data. A Magnetic Resonance (MR) image is defined herein as being the reconstructed two or three dimensional visualization of anatomic data contained within the magnetic resonance imaging data.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
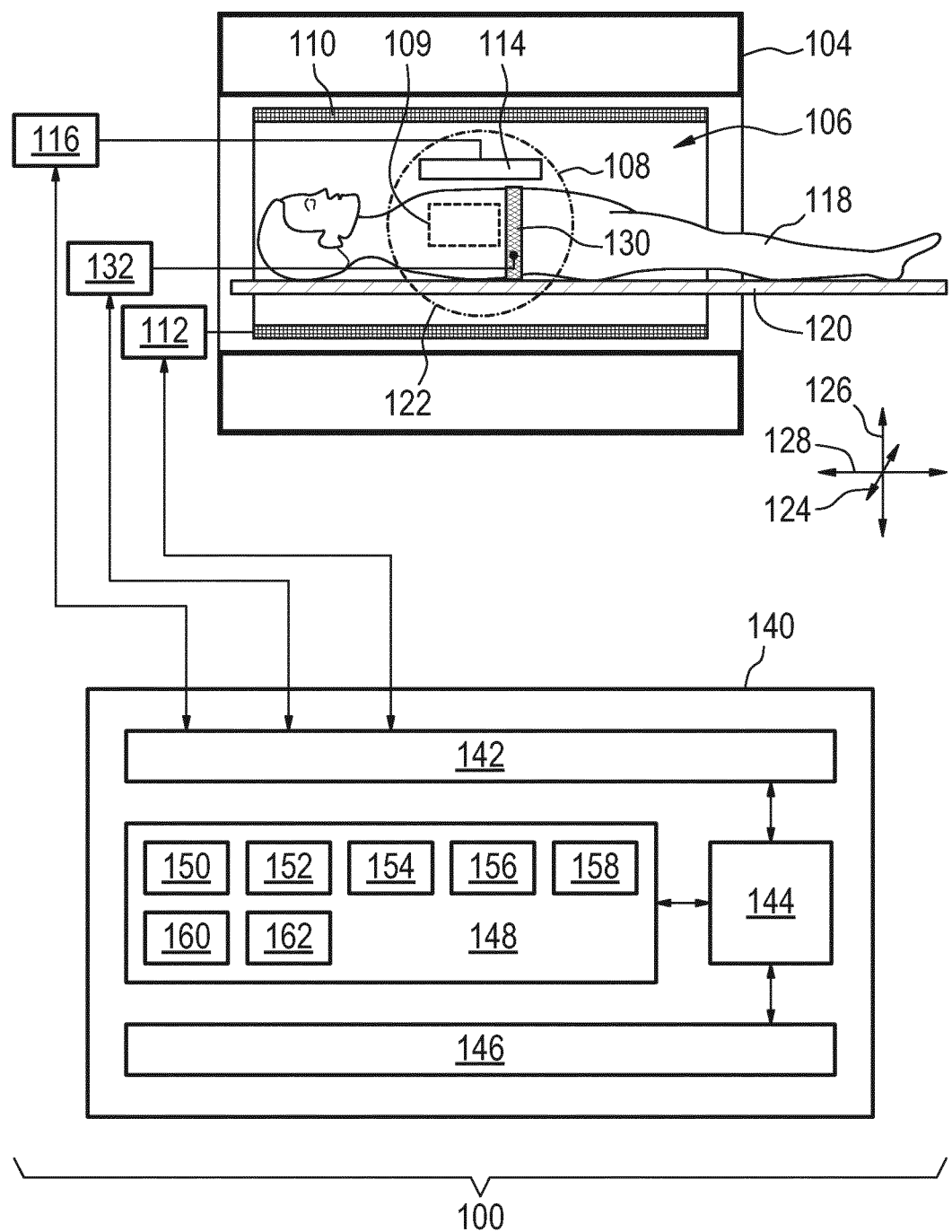
FIG. 1 illustrates an example of a magnetic resonance imaging system.

FIG. 1 shows an example of a magnetic resonance imaging system 100 with a magnet 104. The magnet 104 is a superconducting cylindrical type magnet with a bore 106 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy or radiotherapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging. An imaging region of interest 109 is shown within the imaging zone 108. A subject 118 is shown as being supported by a subject support 120 such that at least a portion of the subject 118 is within the imaging zone 108 and the imaging region of interest 109.

The magnetic resonance imaging system is further shown as containing an optional respiratory belt 130 wrapped around the thorax of the subject 118 which is connected to a respiratory belt controller 132 that is able to generate data in response to the respiratory belt 130 expanding and contracting.

The entire imaging zone 108 is also optionally a navigator region of interest 122. In this example the entire imaging zone 108 can be used to generate a low resolution image which can be used to generate a two-dimensional navigator. The subject 118 is shown as laying on the subject support 120. The arrows labeled 124, 126, and 128 are the x-axis 124, the y-axis 126 and the z-axis 128. The x-axis 124 is intended to be straight in and out of the FIG. It is shown slightly tilted so that the axis 124 is actually visible. The magnetic resonance data acquired from the navigator region of interest 122 can be for example projected onto the x 124, z 128 plane. The entire magnetic resonance data can also be projected onto the y 126 and z 128 plane. This provides for coronal and sagittal images approximately of the subject 118. These low resolution images may be useful in providing a very rapidly acquired but accurate navigator. The imaging region of interest 109 is shown as being smaller than the imaging zone 108 and the navigator region of interest 122.

Within the bore 106 of the magnet there is also a set of magnetic field gradient coils 110 which is used for acquisition of magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientations of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise the transceiver 116 may also represent a separate transmitter and receivers. The radio-frequency coil 114 may also have multiple receive/transmit elements and the radio frequency transceiver 116 may have multiple receive/transmit channels. For example if a parallel imaging technique such as SENSE is performed, the radio-frequency could 114 will have multiple coil elements.

The transceiver 116, the respirator belt 132, and the gradient controller 112 are shown as being connected to a hardware interface 142 of a computer system 140. The computer system further comprises a processor 144 that is in communication with the hardware interface 142, a memory 148, and a user interface 146. The memory 148 may be any combination of memory which is accessible to the processor 144. This may include such things as main memory, cached memory, and also non-volatile memory such as flash RAM, hard drives, or other storage devices. In some examples the memory 148 may be considered to be a non-transitory computer-readable medium.

The memory 148 is shown as containing machine-executable instructions 150. The machine-executable instructions contain commands or instructions which enable the processor 144 to control the operation and function of the magnetic resonance imaging system 100. The computer memory 148 is shown as further containing pulse sequence commands 152. The pulse sequence commands 152 are either instructions or data which may be converted into instructions which enable the processor 144 to control the magnetic resonance imaging system 100 to acquire magnetic resonance data.

The computer memory 148 is further shown as containing a subsequent k-space portion 154 that was acquired by executing the pulse sequence commands 152. The memory 148 is further shown as containing a received motion signal 156 that in this example may include data from the respiratory belt controller 132 and/or two-dimensional navigator data acquired from the navigator region of interest 122. In the case of the received motion signal 156 comprising navigator data the pulse sequence commands 152 may also be adapted for acquiring a low resolution navigator image from the navigator region of interest 122. The motion signal could for example be calculated from the navigator data using the method explained in FIG. 6 below.

The computer memory 148 is further shown as containing a buffer 158 that may be used for storing the receive motion signal and initial k-space portions during a first operational portion. Data stored in the buffer 158 may then be used for constructing a motion phase mapping 160 that is able to relate the receive motion signal 156 to a repetitive motion phase of the subject 118. In this example the repetitive motion phase of the subject would be related to the breathing phase of the subject. The belt 130 and the navigator region of interest 122 can both be used to monitor the expansion and contraction of the subject's lungs 118. The computer memory is further shown as containing a four-dimensional dataset 162 which is constructed by assembling subsequent k-space portions 154.

Figure 2:
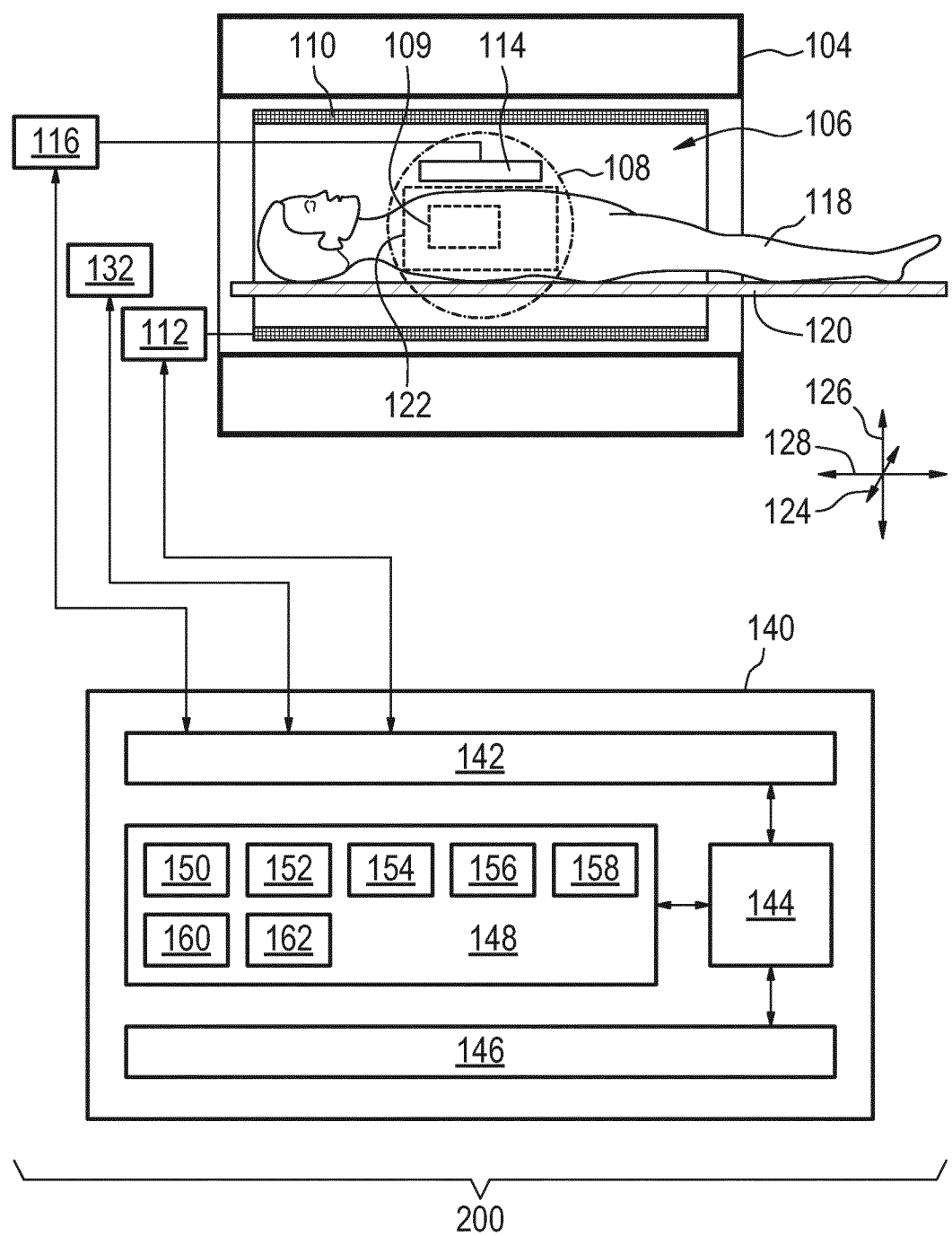
FIG. 2 illustrates a further example of a magnetic resonance imaging system.

FIG. 2 shows a further example of a magnetic resonance imaging system 200 which is similar to that in FIG. 1. The example shown in FIG. 2 differs from that of FIG. 1 in that the navigator region of interest 122 does not encompass the entire imaging zone 108. However, the navigator region of interest 122 is still significantly larger than the imaging region of interest 109. In other examples the region of interest 122 and the imaging region of interest 109 could be the same size. The navigator region of interest 122 can be projected onto the planes for the sagittal and coronal slices as was described in FIG. 1 also. The navigator region of interest 122 is still also large enough that the gross motion of the subject's 118 thorax can still be imaged effectively without the need to precisely define the location of the navigator region of interest 122.

Figure 3:
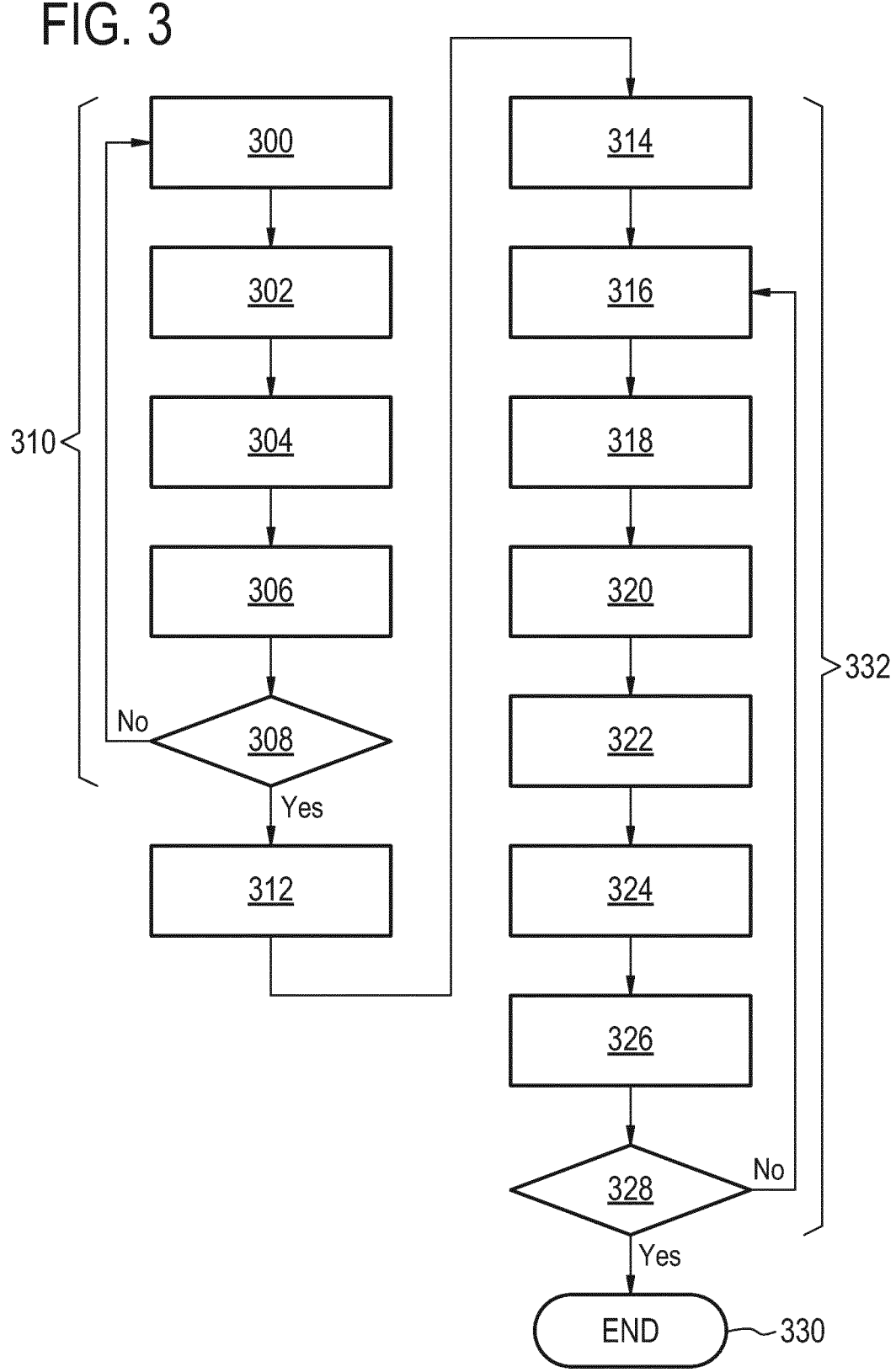
FIG. 3 shows a flow chart which illustrates an example of a method of operating the magnetic resonance imaging system of FIG. 1 or FIG. 2.

FIG. 3 shows a flowchart which illustrates a method of operating the magnetic resonance imaging system 100, 200 of FIG. 1 or 2. The method starts with step 300. In step 300 a motion signal 156 is received. Next in step 302 an initial k-space portion is acquired using the pulse sequence commands 152. Next in step 304 the motion signal 156 and the initial k-space portion are stored in the buffer 158 for each iteration of a first operational phase 310. The first operational portion 310 encompasses steps 300, 302, 304, 306, and 308 as depicted in FIG. 3. Next in step 306 the motion phase mapping 160 is at least partially constructed. Then in step 308 is a question box. The question is "has the motion phase mapping 160 been completed". If the answer is yes the method then proceeds to step 312. If the answer is no the method proceeds back to step 300. In order to completely map the repetitive motion of the subject it may be necessary to repeat the first operational portion 310 a number of times. The acquired initial k-space portion may be varied over the loops of the iteration of 310 to reduce the chance that the same k-space portion is acquired multiple times for the same repetitive motion phase of the subject 118. After the motion phase mapping 160 has been completed step 312 is performed.

In step 312 the motion phase mapping 160 uses the paired initial k-space portions and the accompanying motion signals 156 to assign them to the four-dimensional dataset 162. After step 312 is performed the second operational portion 332 of the method begins. The second operational portion 332 encompasses steps 314, 316, 318, 320, 322, 324, 326 and 328 as depicted in FIG. 3.

After step 312 is performed the method proceeds to step 314. In step 314 the motion signal 156 is received. After this the method proceeds to step 316 where a predicted next motion phase is determined using the motion signal 156 and the motion phase mapping 160. The motion phase mapping 160 may be used in a predictive fashion. For example the receive motion signals 156 from several other iterations may be used so that a trend in the motion signal 156 can be used. This may increase the accuracy of the motion phase mapping 160. Next in step 318 a subsequent k-space portion is selected from the k-space portions of the four-dimensional magnetic resonance dataset 162 using the predicted next motion phase and information about the already recorded k-space portions to select e.g. a missing k-space portion for the predicted next motion phase. Next in step 320 the magnetic resonance imaging system is controlled with pulse sequence commands to acquire the subsequent k-space portion.

Next, during this acquisition the motion signal 156 is re-received in step 322. This, for example, may be performed at the same time, sequentially, or in an interleaved fashion as the magnetic resonance data is acquired for the k-space portion. Next in step 324 a current motion phase is determined using the re-received motion signal and the motion phase mapping 160. The subsequent k-space portion to acquire was selected on a predictive fashion. However the actual phase of the subject may vary slightly from the predicted phase of the subject. In this case the re-received motion signal may be used to verify the proper repetitive motion phase of the subject. Next in step 326 the subsequent k-portion is assigned to the four-dimensional magnetic resonance dataset 162 using the current motion phase. The method then proceeds to step 328. Step 328 is determined if the entire four-dimensional magnetic resonance dataset 162 has been acquired or not. If the answer is yes the method proceeds to step 330 and the method ends. If not the method proceeds back to step 316 and the re-received motion signal is used in step 316 for determining the predicted next motion phase.

Figure 4:
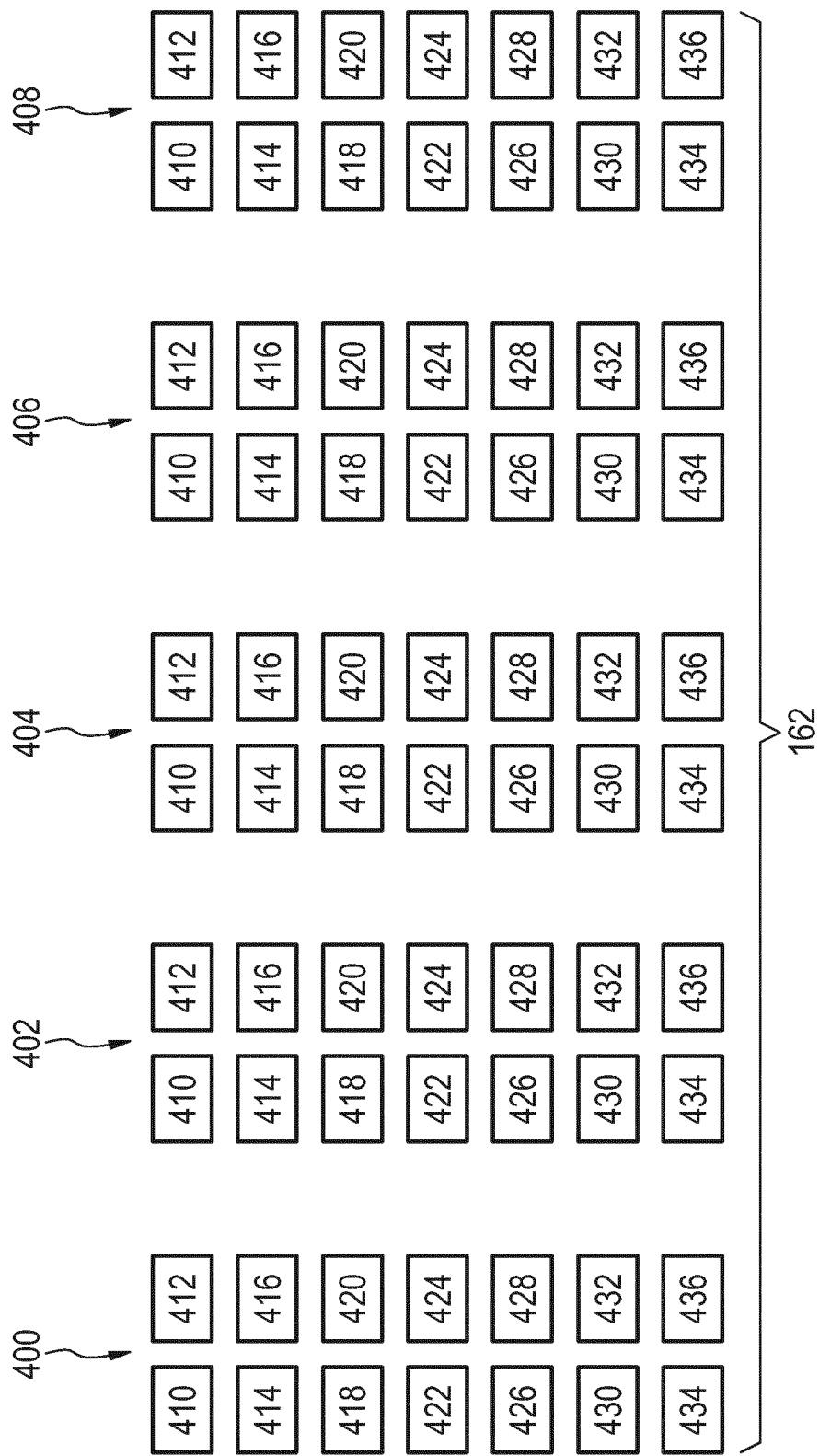
FIG. 4 shows a diagram which models an example of a four dimensional magnetic resonance data set.

FIG. 4 illustrates the structure of the four-dimensional dataset 162. The four-dimensional dataset 162 holds a collection of three-dimensional datasets. In this example there are five three-dimensional datasets. There is a three-dimensional dataset corresponding to a first 400 repetitive motion phase of the subject, there is a three-dimensional dataset corresponding to a second 402 repetitive motion phase of the subject, there is a three-dimensional dataset corresponding to a third 404 repetitive motion phase of the subject, there is a three-dimensional dataset corresponding to a fourth 406 repetitive motion phase of the subject and a three-dimensional dataset corresponding to a fifth 408 repetitive motion phase of the subject. Within each of these three-dimensional datasets 400, 402, 404, 406, 408 there are a number of k-space portions. There are fourteen k-space portions labeled 410, 412, 414, 416, 418, 420, 422, 424, 426, 428, 430, 432, 434, and 436. Each of the k-space portions corresponds to a trajectory in k-space that has either been acquired or will be acquired to complete the four-dimensional dataset 162. When a k-space portion is acquired the motion signal is used to determine to which of the three-dimensional datasets 400, 402, 406, 408, 410, the acquired k-space portion should be appended to.

Figure 5:
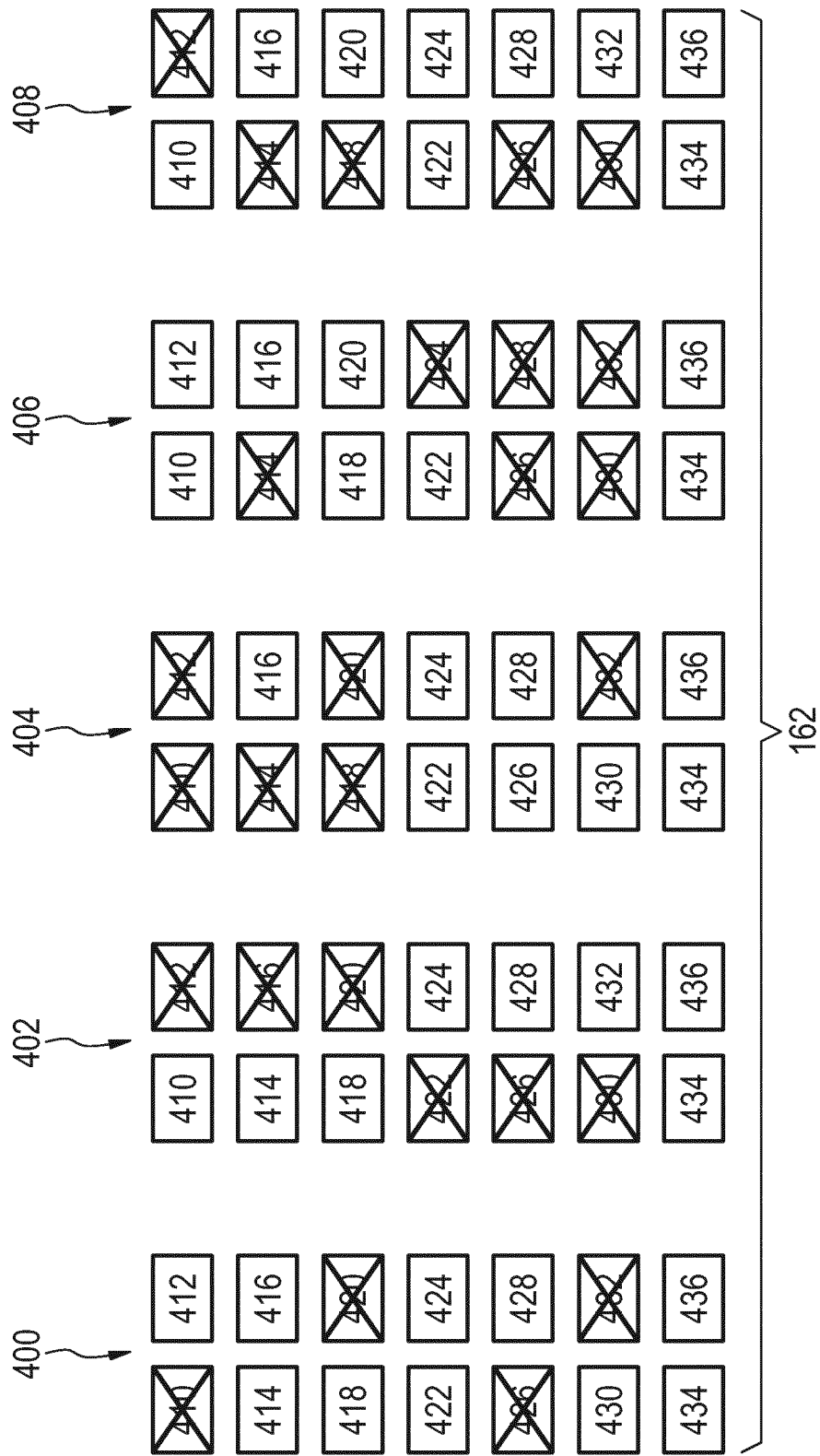
FIG. 5 shows a further view of the four dimensional magnetic resonance data set of FIG. 4.

FIG. 5 illustrates the four-dimensional dataset 162 during the second operational portion 332 of the method illustrated in FIG. 3. k-space portions which have been crossed out with an X have been acquired. k-space portions which are not crossed out with an X still need to be acquired. For example in step 316 the predicted next motion phase might be the fourth 406 repetitive motion phase. In step 318 the algorithm would then select the k-space portion labeled 410, 412, 416, 418, 420, 422, 434, or 436 to acquire next. For example if the thirteenth k-space portion 434 for the fourth phase 406 is selected in step 320 in FIG. 3 this k-space portion 434 would be acquired. After the motion signal has been re-received the algorithm would then verify that the k-space portion 434 should be inserted into the three-dimensional dataset corresponding to the fourth repetitive motion phase 406. In case the re-received motion signal indicates a different motion phase, it will be assigned accordingly and can be stored in the corresponding (correct) phase. This could result in filling a a not yet acquired k-space portion, replacing/combining with an already acquired k-space portion, e.g. by averaging or ignoring it.

Figure 6:
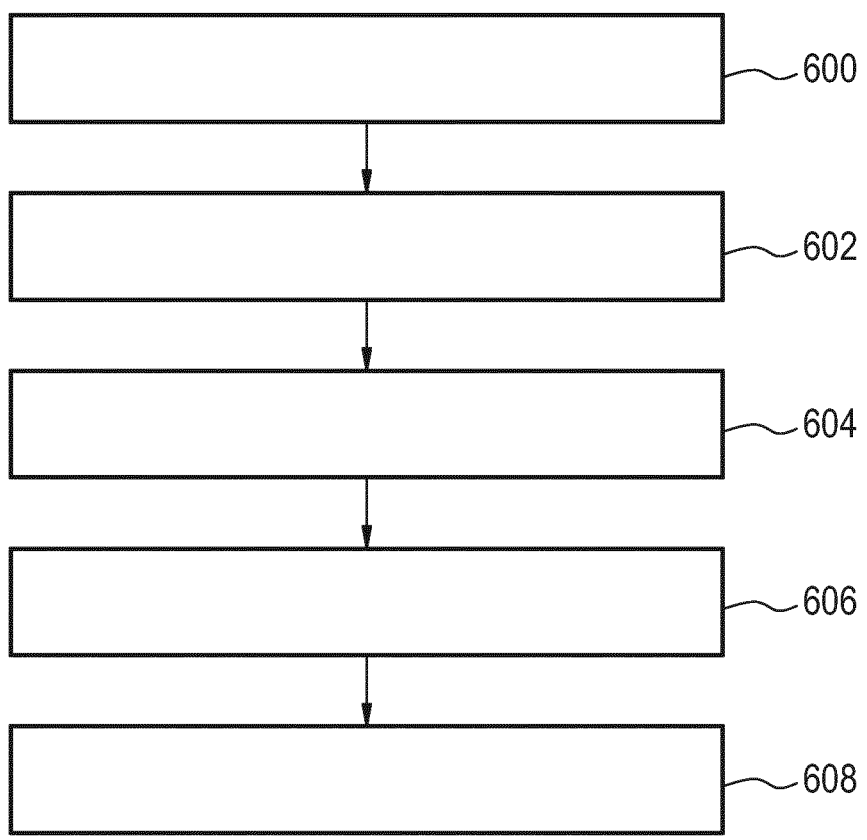
FIG. 6 shows a flow chart which illustrates a further method of operating the magnetic resonance imaging system of FIGS. 1 and 2.

FIG. 6 shows a flowchart of an alternative method 600 of operating the magnetic resonance imaging systems 100, 200 shown in FIGS. 1 and 2. The pulse sequence commands may be configured for acquiring imaging magnetic resonance data from an imaging region of interest. The pulse sequence commands are further configured to control the magnetic resonance imaging system to acquire 2D magnetic resonance imaging navigator data from a navigator region of interest using the pulse sequence commands. The navigator region of interest is the same size or larger than the imaging region of interest. The navigator region of interest comprises the imaging region of interest.

Execution of the machine-executable instructions 150 cause the processor to control the magnetic resonance imaging system with the pulse sequence commands to acquire two-dimensional magnetic resonance imaging navigator data and imaging magnetic resonance data. Next in step 602 a two-dimensional navigator image is reconstructed using the two-dimensional magnetic resonance imaging navigator data. The two-dimensional navigator image may be positioned as well as described in FIGS. 1 and 2. The two-dimensional magnetic resonance imaging navigator data may be acquired from the fourth imaging zone 108 such as is illustrated in FIG. 1 or from the navigator region of interest 122 illustrated in FIG. 2. Next in step 604 a navigator registration is calculated by registering the two-dimensional navigator image to at least one other two-dimensional navigator image from a previous repetition. Next in step 606 a motion signal 156 is at least partially calculated using the navigator registration. Finally in step 608 the motion signal is assigned to the imaging magnetic resonance data. The imaging magnetic resonance data may be reconstructed into an image or may be combined with other imaging magnetic resonance data later to combine an image for the corresponding motion signal.

DETAILED DESCRIPTION OF THE INVENTION

In conclusion, various clinical tasks are facilitated or require a 4D-MR-scan of anatomical structures. Examples for such tasks are:
  Visualization and diagnosis of regularly moving organs (e.g. heart)
  Radiotherapy planning with integrated motion related dose calculation
  Therapy monitoring (e.g. MR-Linac) and control of irradiation depending on motion (state).

Current clinical 4D-MRI sequences are either based on a prospectively triggered image acquisition or employ retrospective image based sorting into motion states. A drawback of the triggered acquisition is the need for a additional monitoring/triggering device, e.g. respiration monitor belt, camera or an MR navigator, which complicates the workflow. Another disadvantage of the triggered acquisition is that it cannot adapt well to irregular breathing patterns and may have very low efficiency for some patients.

The retrospective image based sorting on the other hand does not guarantee that the acquired 4D dataset will be complete (i.e. contains all respiratory phases for each slice). For instance, an imaging sequence which is longer than the available pre-beam time slot hampers efficient operation/use of the MR-Linac. The proposed method is able to acquire the 4D image efficiently without the need for a triggering device.
Current 4D methods do not cope well with irregular movements. Using the proposed method, these can be detected and used for a reliable beam control.

Examples may provide for a method which records high temporal but low spatial resolution images to create an integral motion state monitoring information (navigator) interleaved with high resolution 2D images at varying spatial locations. The high resolution spatio-temporal space is then incrementally filled employing the navigator images. Missing points in that space, i.e. images at a certain motion state/location, can then be filled in an intelligent/fast fashion by specifically recording the respective slice at the specific motion state.

In the first phase (first operational portion), the interleaved acquisition of navigator and high resolution images is performed according to a fixed scheme. The slice index of the high resolution image is set according to a predefined slice sequence (e.g. the standard multi-slice TSE slice ordering).

The navigator images recorded during this first phase are analysed until the average breathing cycle is fully covered with sufficient statistical evidence. I.e. the end of the first phase is reached when it is possible to assign each new navigator image to a motion state, which has previously been recorded.

In one realization the navigator can consist of the projection of the imaging volume (or imaging zone) onto one slice, which has the advantages that:
  no specific navigator planning (as e.g. with pencil beams) is needed as the same FOV as for the high resolution images can be used
  the projection across many "slices" reduces noise
  fast acquisition possible (e.g. 25 ms per navigator image)
  2D navigator image information can be used to implement more robust motion state analysis Furthermore, it is then also possible to make predictions on the probability of which motion state will be acquired in the next navigator. (This is done by computing a 2D histogram for pairs of subsequent motion states which have been observed so far.) In a regular motion pattern such a 2D histogram would show sharp peaks, as motion states will follow the same sequence and hence a certain current motion phase will be followed by the same motion phase each repetition. In more irregular motion patterns the histogram may look more blurred. In those cases the histogram may provide for information about outliers and how likely a certain motion state will occur. In case of a more irregular motion pattern, the motion phase mapping (e.g. the 2D histogram) may be used to predict the most dominant pattern in order to acquire all k-space portions to fill the 4D dataset covering this most dominant pattern. However, it may also be used to predict when outliers may occur in order to create a 4D dataset comprising the outliers as well. This could for example be relevant for treatment planning. One option is to stop treatment when an outlier occurs. Alternatively, the existence of outliers could be taken into account during treatment planning, e.g. by using treatment margins.
Instead of 2D histograms also longer sequences of motion states could be used to predict a subsequent motion phase. In addition to that, other alternatives, like e.g. Bayesian inference networks could be used.
In case an incorrect prediction is made, the k-space portions acquired as a result of this prediction may for example be discarded. Alternatively, if the k-space portions appear to be related to a motion phase for which these data are still lacking, the k-space portions may be assigned to this latter motion phase.
At this point in time all high resolution images that have been acquired so far can be assigned to motion states. I.e. the state of completion of the planned 4D scan can be assessed.

Now the second phase (second operational portion) of the method starts. In this phase a dynamic selection of the slice index of the high spatial-resolution image is used with the aim to fill in all missing data of the planned 4D scan as quickly as possible. The selection of the next high resolution slice is based on the prediction of the next motion state from the current navigator image. Other criteria like a minimum TR between excitations of the same slice may also be taken into account.

If further speed-up is needed, missing motion states can be compensated/filled by e.g. image interpolation in combination with elastic image registration.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS

- 100 magnetic resonance imaging system
- 104 magnet
- 106 bore of magnet
- 108 imaging zone
- 109 imaging region of interest
- 110 magnetic field gradient coils
- 112 magnetic field gradient coil power supply
- 114 radio-frequency coil
- 116 transceiver
- 118 subject
- 120 subject support
- 122 navigator region of interest
- 124 x-axis
- 126 y-axis
- 128 z-axis
- 130 respiratory belt
- 132 respiratory belt controller
- 140 computer system
- 142 hardware interface
- 144 processor
- 146 user interface
- 148 computer memory
- 150 machine executable instructions
- 152 pulse sequence commands
- 154 subsequent k-space portion
- 156 motion signal
- 158 buffer
- 160 motion phase mapping
- 162 four dimensional data set
- 200 magnetic resonance imaging system
- 300 receive a motion signal descriptive of the repetitive motion phase
- 302 acquire an initial k-space portion using the pulse sequence commands
- 304 store the motion signal and the initial k-space portion in a temporary buffer for each iteration of the first operational portion
- 306 at least partially construct a motion phase mapping between the motion signal and the repetitive motion phase
- 308 Is the motion phase mapping complete?
- 310 first operational portion
- 312 assign the initial k-space portion for each iteration of the first operational portion in the temporary buffer to the four dimensional magnetic resonance data set using the motion phase mapping
- 314 receive the motion signal
- 316 determine a predicted next motion phase using the motion signal and the motion phase mapping
- 318 select a subsequent k-space portion from the k-space portions of the four dimensional magnetic resonance data set using the predicted next motion phase
- 320 acquire the subsequent k-space portion using the pulse sequence commands
- 322 re-receive the motion signal
- 324 determine a current motion phase using the re-received motion signal and the motion phase mapping
- 326 assign the subsequent k-space portion to the four dimensional magnetic resonance data set using the current motion phase
- 328 Has all of the four dimensional magnetic resonance data set been acquired?
- 400 first repetitive motion phase of the subject
- 402 second repetitive motion phase of the subject
- 404 third repetitive motion phase of the subject
- 406 fourth repetitive motion phase of the subject
- 408 fifth repetitive motion phase of the subject
- 410 first k-space portion
- 412 second k-space portion
- 414 third k-space portion
- 416 fourth k-space portion
- 418 fifth k-space portion
- 420 sixth k-space portion
- 422 seventh k-space portion
- 424 eighth k-space portion
- 426 ninth k-space portion
- 428 tenth k-space portion
- 430 eleventh k-space portion
- 432 twelfth k-space portion
- 434 thirteenth k-space portion
- 436 fourteenth k-space portion

The invention claimed is:

1. A magnetic resonance imaging system comprising:

a processor;

a tangible non-transitory computer readable medium that stores instructions, which when executed by the processor, causes the processor, during a first operational portion to iteratively:

receive a motion signal descriptive of the repetitive motion phase;

acquire an initial k-space portion using pulse sequence commands configured for acquiring a four dimensional magnetic resonance data set from an imaging region of interest, wherein: the three dimensional data magnetic resonance data sets are further at least divided into and indexed by k-space portions; the acquisition of the four dimensional magnetic resonance data set is at least divided into three dimensional data magnetic resonance data sets indexed by a repetitive motion phase of the subject; and the initial k-space portion is selected from the k-space portions;

store the motion signal and the initial k-space portion in a buffer for each iteration of the first operational portion;

at least partially construct a motion phase mapping between the motion signal and the repetitive motion phase; and continue the first operational portion until the motion phase mapping is complete;

wherein execution of the machine executable instructions further causes the processor to assign the initial k-space portion for each iteration of the first operational portion in a temporary buffer to the four dimensional magnetic resonance data set using the motion phase mapping;

wherein execution of the machine executable instructions further causes the processor during a second operational portion to iteratively:

receive the motion signal;

determine a predicted next motion phase using the motion signal and the motion phase mapping;

select a subsequent k-space portion from the k-space portions of the four dimensional magnetic resonance data set using the predicted next motion phase;

acquire the subsequent k-space portion using the pulse sequence commands and;

re-receive the motion signal;

determine a current motion phase using the re-received motion signal and the motion phase mapping;

assign the subsequent k-space portion to the four dimensional magnetic resonance data set using the current motion phase;

repeat the second operational portion until the k-space portions for each repetitive motion phase has been assigned, wherein the re-received motion signal is used for determining the predicted next motion phase; and construct a four dimensional magnetic resonance image using the k-space portions acquired during the first operational portion and the k-space portions acquired during the second operational portion.

2. The magnetic resonance imaging system of claim 1, wherein the pulse sequence commands are configured to control the magnetic resonance imaging system to acquire two dimensional (2D) magnetic resonance imaging navigator data from a navigator region of interest using the pulse sequence commands, wherein the navigator region of interest is the same size or larger than the imaging region of interest, and wherein the navigator region of interest comprises the imaging region of interest, and wherein receiving a motion signal descriptive of the repetitive motion phase comprises at least partially calculating the motion signal using the 2D magnetic resonance imaging navigator data.

3. The magnetic resonance imaging system of claim 2, wherein calculating the motion signal using the 2D magnetic resonance imaging navigator data comprises:

reconstructing a 2D navigator image using the 2D magnetic resonance imaging navigator data;

calculating a navigator registration by registering the 2D navigator image to at least one other 2D navigator image from another iteration of the other iterations of the first operational portion; and calculating the motion signal at least partially using the navigator registration.

4. The magnetic resonance imaging system of claim 2, the magnetic resonance imaging system comprises an imaging volume, wherein the navigator region of interest is equivalent to the imaging volume.

5. The magnetic resonance imaging system of claim 4, wherein the navigator region of interest comprises a two-dimensional span, wherein the navigator region of interest comprises a thickness perpendicular to the two-dimensional span, wherein the two-dimensional span has a thickness perpendicular to the two-dimensional span.

6. The magnetic resonance imaging system of claim 1, wherein the motion signal comprises any one of the following: camera data, one-dimensional magnetic resonance imaging (MRI) navigator data, two-dimensional MRI navigator data, respiration monitor belt data, and pencil navigator data.

7. The magnetic resonance imaging system of claim 1, wherein a current motion phase is determined using a trajectory calculated using motion signal data received during previous iterations of the second operational portion.

8. The magnetic resonance imaging system of claim 1, wherein the repetitive motion phase comprises a respiratory phase.

9. The magnetic resonance imaging system of claim 1, wherein the k-space portion is any one of the following: k-space data for a two-dimensional slice, a portion of k-space data for a two-dimensional slice, and a portion of k-space data for a three-dimensional volume.

10. The magnetic resonance imaging system of claim 1, wherein assigning the subsequent k-space portion for each iteration of the second operational portion to the four dimensional magnetic resonance data set comprises any one of the following: copying the subsequent k-space portion to the four dimensional magnetic resonance data set, averaging the subsequent k-space portion with existing data in the four dimensional magnetic resonance data set, replacing existing data in the four dimensional magnetic resonance data set, and ignoring the subsequent k-space portion.

11. The magnetic resonance imaging system of claim 1, wherein the assigning of the initial k-space portion for each iteration of the first operational portion in a temporary buffer to the four dimensional magnetic resonance data set using the motion phase mapping comprises any one of the following: copying the initial k-space portion to the four dimensional magnetic resonance data set, averaging the initial k-space portion with existing data in the four dimensional magnetic resonance data set, replacing existing data in the four dimensional magnetic resonance data set, and ignoring the initial k-space portion.

12. The magnetic resonance imaging system of claim 1, wherein any one of the following: wherein the initial k-space portion is selected according to a predetermined sequence and wherein the k-space portion is selected at random.

13. A tangible, non-transitory computer readable medium that stores instructions, which when executed by a processor, causes the processor, during a first operational portion, to iteratively:

receive a motion signal descriptive of a repetitive motion phase of a subject;

acquire an initial k-space portion using pulse sequence commands to control the magnetic resonance imaging system, wherein the pulse sequence commands are configured for acquiring a four dimensional magnetic resonance data set from an imaging region of interest, wherein the acquisition of the four dimensional magnetic resonance data set is at least divided into three dimensional data magnetic resonance data sets indexed by a repetitive motion phase of the subject, wherein the three dimensional data magnetic resonance data sets are further at least divided into and indexed by k-space portions, wherein the initial k-space portion is selected from the k-space portions;

store the motion signal and the initial k-space portion in a buffer for each iteration of the first operational portion;

at least partially construct a motion phase mapping between the motion signal and the repetitive motion phase; and continue the first operational portion until the motion phase mapping is complete;

wherein the instructions further cause the processor to assign the initial k-space portion for each iteration of the first operational portion in the temporary buffer to the four dimensional magnetic resonance data set using the motion phase mapping;

wherein the instructions further cause the processor, during a second operational portion, to iteratively:

receive the motion signal;

determine a predicted next motion phase using the motion signal and the motion phase mapping, i.e. motion model;

select a subsequent k-space portion from the k-space portions of the four dimensional magnetic resonance data set using the predicted next motion phase;

acquire the subsequent k-space portion using the pulse sequence commands and;

re-receive the motion signal;

determine a current motion phase using the re-received motion signal and the motion phase mapping;

assign the subsequent k-space portion to the four dimensional magnetic resonance data set using the current motion phase;

repeat the second operational portion until the k-space portions for each repetitive motion phase has been assigned, wherein the re-received motion signal is used for determining the predicted next motion phase; and construct a four dimensional magnetic resonance image using the k-space portions acquired during the first operational portion and the k-space portions acquired during the second operational portion.

14. A method for operating a magnetic resonance imaging system, wherein the method comprises, during a first operational portion, iteratively:

receiving a motion signal descriptive of a repetitive motion phase of a subject;

acquiring an initial k-space portion using pulse sequence commands to control the magnetic resonance imaging system, wherein the pulse sequence commands are configured for acquiring a four dimensional magnetic resonance data set from an imaging region of interest, wherein the acquisition of the four dimensional magnetic resonance data set is at least divided into three dimensional data magnetic resonance data sets indexed by a repetitive motion phase of the subject, wherein the three dimensional data magnetic resonance data are further at least divided into and indexed by k-space portions, wherein the initial k-space portion is selected from the k-space portions;

storing the motion signal and the initial k-space portion in a buffer for each iteration of the first operational portion;

at least partially constructing a motion phase mapping between the motion signal and the repetitive motion phase; and continuing the first operational portion until the motion phase mapping is complete;

wherein the method further comprises assigning the initial k-space portion for each iteration of the first operational portion in the temporary buffer to the four dimensional magnetic resonance data set using the motion phase mapping;

wherein the method further comprises, during a second operational portion, iteratively:

receiving the motion signal;

determining a predicted next motion phase using the motion signal and the motion phase mapping;

selecting a subsequent k-space portion from the k-space portions of the four dimensional magnetic resonance data set using the predicted next motion phase;

acquiring the subsequent k-space portion using the pulse sequence commands;

re-receiving the motion signal;

determining a current motion phase using the re-received motion signal and the motion phase mapping;

assigning the subsequent k-space portion to the four dimensional magnetic resonance data set using the current motion phase;

repeating the second operational portion until the k-space portions for each repetitive motion phase has been assigned, wherein the re-received motion signal is used for determining the predicted next motion phase; and constructing a four dimensional magnetic resonance image using the k-space portions acquired during the first operational portion and the k-space portions acquired during the second operational portion.

15. The tangible, non-transitory computer readable medium of claim 14, wherein the pulse sequence commands are configured to control the magnetic resonance imaging system to acquire two dimensional (2D) magnetic resonance imaging navigator data from a navigator region of interest using the pulse sequence commands, wherein the navigator region of interest is the same size or larger than the imaging region of interest, and wherein the navigator region of interest comprises the imaging region of interest, and wherein receiving a motion signal descriptive of the repetitive motion phase comprises at least partially calculating the motion signal using the 2D magnetic resonance imaging navigator data.

16. The tangible, non-transitory computer readable medium of claim 15, wherein calculating the motion signal using the 2D magnetic resonance imaging navigator data comprises:

reconstructing a 2D navigator image using the 2D magnetic resonance imaging navigator data;

calculating a navigator registration by registering the 2D navigator image to at least one other 2D navigator image from another iteration of the other iterations of the first operational portion; and calculating the motion signal at least partially using the navigator registration.

17. The tangible, non-transitory computer readable medium of claim 15, wherein a current motion phase is determined using a trajectory calculated using the motion signal data received during previous iterations of the second operational portion.

18. The tangible, non-transitory computer readable medium of claim 15, wherein the repetitive motion phase comprises a respiratory phase.

19. The tangible, non-transitory computer readable medium of claim 15, wherein the k-space portion is any one of the following: k-space data for a two-dimensional slice, a portion of k-space data for a two-dimensional slice, and a portion of k-space data for a three-dimensional volume.

* * * * *